US009782330B2

(12) United States Patent
Xu et al.

(10) Patent No.: US 9,782,330 B2
(45) Date of Patent: Oct. 10, 2017

(54) MOUTHWASH PRODUCT AND METHOD OF MAKING AND USING THE PRODUCT

(71) Applicant: COLGATE-PALMOLIVE COMPANY, New York, NY (US)

(72) Inventors: Guofeng Xu, Plainsboro, NJ (US); Steven Miller, Skillman, NJ (US); Jennifer Gronlund, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 160 days.

(21) Appl. No.: 14/365,122

(22) PCT Filed: Dec. 19, 2012

(86) PCT No.: PCT/US2012/070578
§ 371 (c)(1),
(2) Date: Jun. 13, 2014

(87) PCT Pub. No.: WO2013/096427
PCT Pub. Date: Jun. 27, 2013

(65) Prior Publication Data
US 2015/0114436 A1      Apr. 30, 2015

Related U.S. Application Data

(60) Provisional application No. 61/577,572, filed on Dec. 19, 2011.

(51) Int. Cl.
| B08B 3/10 | (2006.01) |
| B08B 13/00 | (2006.01) |
| A61K 8/02 | (2006.01) |
| A61Q 11/00 | (2006.01) |
| A61K 8/368 | (2006.01) |
| A61K 8/19 | (2006.01) |

(52) U.S. Cl.
CPC ............. *A61K 8/0283* (2013.01); *A61K 8/19* (2013.01); *A61K 8/368* (2013.01); *A61Q 11/00* (2013.01); *A61K 2800/87* (2013.01)

(58) Field of Classification Search
CPC .... A61K 2800/87; A61K 8/0283; A61K 8/19; A61K 8/368; A61Q 11/00
See application file for complete search history.

(56) References Cited

U.S. PATENT DOCUMENTS

| 3,535,421 A | 10/1970 | Briner et al. |
| 3,678,154 A | 7/1972 | Widder |
| 4,885,155 A | 12/1989 | Parran, Jr. et al. |
| 5,624,906 A * | 4/1997 | Vermeer .................. A61K 8/60 514/23 |
| 2010/0166833 A1 | 7/2010 | Gavish et al. |

FOREIGN PATENT DOCUMENTS

| CN | 101999990 | 4/2011 |
| KR | 2004008011 A * | 9/2004 |
| WO | WO 99/59539 | 11/1999 |
| WO | WO2006021966 | 3/2006 |
| WO | WO 2009/027478 | 3/2009 |

OTHER PUBLICATIONS

Abstract of KR20040080111A dated Sep. 2004.*
Abstract of KR2004008011A dated Sep. 2004.*
DeSilva, Frank, "Activated Carbon Filtration," Water Quality Products Magazine, Jan. 2000, Retrieved from the Internet at URL: http://www.watertreatmentguide.com/activated_carbon_filtration.htm.
International Search Report and the Written Opinion issued in International Application PCT/US2012/70578 mailed Feb. 11, 2014. WO.
Chemicals Used in Food Processing, publication 1274 by the National Academy of Sciences, pp. 63-258 US.
Mintel; Dec. 2010, "Spearmint Breath Blast Mouthrinse", XP002718640, Database accession No. 1455766, Product Description Ingredients US.
Soni, M G, et al: "Safety assessment of esters of p-hydroxybenzoic acid (parabens)", Food and Chemical Toxicology, Pergamon, GB, vol. 43, No. 7, Jul. 1, 2005, pp. 985-1015, XP027602416, ISSN: 0278-6915, [retrieved on Jul. 1, 2005,], "1.2.2 Uses in cosmetics", "3. Risk evaluation" US.

* cited by examiner

*Primary Examiner* — Douglas Lee

(57) ABSTRACT

Described herein are systems for removing selected components, e.g., stabilizing agents or preservatives, from a liquid composition just prior to use, using activated charcoal or an affinity matrix filter, together with variant and alternative designs, methods of making and using the product, and components thereof.

14 Claims, No Drawings

US 9,782,330 B2

MOUTHWASH PRODUCT AND METHOD OF MAKING AND USING THE PRODUCT

CROSS-REFERENCE TO RELATED PATENT APPLICATIONS

The present application is a U.S. national stage entry under 35 U.S.C. §371 of Patent Cooperation Treaty Patent Application No. PCT/US2012/70578, filed Dec. 19, 2012, which claims priority to U.S. Provisional Patent Application No. 61/577,572, filed Dec. 19, 2011, the entirety of which is incorporated herein by reference.

BACKGROUND

High alcohol mouthwash may be undesirable for children, alcoholics, people suffering from dry mouth, and people who wish to avoid alcohol for religious reasons. Low alcohol or alcohol-free mouthwash formulations, however, typically require the use of a preservative such as sodium benzoate or methylparaben to avoid microbial contamination of the product during storage. While such preservatives are generally recognized as safe, many consumers may nevertheless wish to avoid ingestion or contact with such compounds or may prefer preservative-free products.

There is a consumer demand for a mouthwash product that is suitable for long term storage without spoilage or microbial contamination, but minimizes consumer exposure to alcohol or preservatives.

SUMMARY

To address this demand, we have developed a novel system for removing selected components, e.g., preservatives, from a mouthwash just prior to use, using an activated charcoal or affinity matrix filter.

The invention therefore provides, in one embodiment, a mouthwash product comprising a container holding a mouthwash formulation, the container comprising a filter which filters the mouthwash just prior to use,
  wherein the mouthwash formulation is orally acceptable and comprises a stabilizing agent or a preservative, e.g., selected from $C_{1-4}$ alkyl esters of para-hydroxybenzoic acid (parabens, e.g. methylparaben) and benzoic acid, in free or base addition salt form (e.g., sodium benzoate); and
  the filter comprises material capable of removing the preservative from the mouthwash formulation prior to use, e.g., the filter comprising activated carbon or affinity beads or affinity matrix. The mouthwash may optionally further comprise fluoride ions, calcium ions, buffering agents, and/or other active agents that would not be filtered out by the filter.

In a further embodiment, the container further comprises a matrix distal to the filter comprising sparingly soluble ingredients which are imparted to the mouthwash after filtering and just prior to use, e.g., sparingly soluble flavorings, plant extracts, and/or antibacterial agents, e.g., comprising one or more of epigallocatechin 3-gallate (EGCG), magnolol, thymol, eucalyptol, hexetidine, triclosan, methyl salicylate, menthol, or chlorhexidine gluconate.

In another embodiment, the invention provides a method of dispensing a mouthwash comprising a preservative, e.g., as described above, comprising the step of filtering the mouthwash to remove the preservative just prior to use, and optionally adding to the mouthwash one or more sparing soluble ingredients after filtering and just prior to use.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention provides a mouthwash product (Product 1) comprising a container holding a mouthwash formulation, the container comprising a filter which filters the mouthwash just prior to use,
  wherein the mouthwash formulation is orally acceptable and comprises a preservative, e.g., selected from $C_{1-4}$ alkyl esters of para-hydroxybenzoic acid (parabens, e.g. methylparaben) and benzoic acid, in free or base addition salt form (e.g., sodium benzoate); and
  the filter comprises material capable of removing the preservative from the mouthwash formulation prior to use, e.g., the filter comprising activated carbon or affinity beads or affinity matrix.

For example, the invention provides
  1.1. Product 1 comprising a pump which pumps the mouthwash through the filter and out the aperture.
  1.2. Product 1 wherein the mouthwash is dispensed by pouring the mouthwash through the filter and out the aperture.
  1.3. Any of the foregoing products wherein the connection to the filter is sealed when not in use, e.g., by a ring twist closure.
  1.4. Any of the foregoing products wherein the mouthwash further comprises fluoride ions, calcium ions, zinc ions, buffering agents, and/or other active agents that would not be filtered out by the filter.
  1.5. Any of the foregoing products wherein the container further comprises a matrix distal to the filter comprising sparingly soluble ingredients which are imparted to the mouthwash after filtering and just prior to use, e.g., sparingly soluble flavorings, plant extracts, and/or antibacterial agents, e.g., comprising one or more ingredients selected from encapsulated or modified epigallocatechin 3-gallate (EGCG), magnolol, thymol, eucalyptol, hexetidine, triclosan, methyl salicylate, menthol, encapsulated or modified chlorhexidine gluconate, spearmint oil, cinnamon oil, peppermint oil, clove oil, bay oil, thyme oil, cedar leaf oil, oil of nutmeg, oil of sage, and oil of bitter almonds.
  1.6. Any of the foregoing products wherein the mouthwash formulation comprises an orally acceptable antiplaque agent, e.g., selected from stannous, copper, magnesium and strontium salts, and mixtures thereof.
  1.7. Any of the foregoing products wherein the mouthwash formulation comprises a desensitizing agent, e.g., selected from potassium chloride, potassium nitrate, strontium salts, and mixtures thereof.
  1.8. Any of the foregoing products wherein the mouthwash formulation comprises one or more antioxidants, e.g., selected from butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the invention provides a method of dispensing a mouthwash comprising a preservative, e.g., selected from $C_{1-4}$ alkyl esters of para-hydroxybenzoic acid (parabens, e.g. methylparaben) and benzoic acid, in free or base addition salt form (e.g., sodium benzoate); comprising the step of filtering the mouthwash to remove the preservative just prior to use, and optionally adding to the mouthwash one or more sparingly soluble ingredients after filtering and just prior to use.

In another embodiment, the invention provides methods of tooth whitening or cleaning or of treating conditions of the oral cavity such as gingivitis, dental plaque or halitosis, or reducing demineralization of the enamel, comprising applying a mouthwash dispensed in accordance with the foregoing paragraph to the oral cavity, e.g., by rinsing the mouth with the activated mouthwash for a period of 15 seconds to one minute and then spitting the mouthwash out.

Orally Acceptable:

All ingredients for use in the mouthwash formulations described herein should be orally acceptable. By "orally acceptable" as the term is used herein is meant an ingredient which is present in the formulation as described in an amount and form which does not render the formulation unsafe, unpalatable or otherwise unsuitable for use in the oral cavity.

Active Agents:

The effective concentration of the active ingredients used herein will depend on the particular agent and the delivery system used. Actives, when present in compositions of the invention, are provided in effective amounts. Fluoride where present in a mouthwash may be present at levels of for example about 25 to about 250 ppm. Levels of antibacterial agents in a mouthwash will vary similarly, e.g., in some embodiments, antimicrobial agent is present at a concentration of from about 0.001 to about 1%, by weight, e.g. where the antimicrobial agent is cetylpyridinium chloride, e.g., at a concentration of about 0.05%, by weight, or where the antibacterial agent is triclosan, e.g. at a concentration of about 0.03% by weight.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention thus may contain a source of fluoride ions or fluorine-providing ingredient in amounts sufficient to supply about 25 to about 250 ppm fluoride. Weights of fluoride salts to provide the appropriate level of fluoride ion will obviously vary based on the weight of the counter ion in the salt.

The sparingly soluble agents added to the mouthwash after filtering in one embodiment above may optionally comprise flavorings. Flavor agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

In some embodiments, the methods comprise the step of rinsing the oral cavity with a mouthwash composition as described above. In some embodiments, 5 ml or more of the composition is gargled. In some embodiments, 10 ml or more is used. In some embodiments, 10-50 ml is used. In some embodiments, 15-25 ml or more is used. In some embodiments, 15 ml or more is used. In some embodiments, the individual gargles with the composition multiple times per day. In some embodiments, the individual gargles with the composition on multiple days. In some embodiments, the individual gargles with the composition every 4 to 6 hours up to 6 times per day.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention claimed is:

1. A mouthwash product comprising a container, wherein the container comprises a compartment holding a liquid mouthwash formulation, and a filter connected to the compartment configured to filter the liquid formulation prior to use, and connected to the filter, an aperture for dispensing,
   wherein the liquid formulation is orally acceptable and comprises a preservative;
   the filter comprises a material capable of removing the preservative from the liquid formulation prior to use; wherein the compartment holding the liquid formulation and the filter are arranged such that the liquid formulation is passed through the filter during dispensing of the liquid mouthwash formulation;
   the liquid mouthwash formulation further comprises fluoride ions, calcium ions, zinc ions, buffering agents, and/or other active agents that would not be filtered out by the filter; and
   the preservative is selected from $C_{1-4}$ alkyl esters of para-hydroxybenzoic acid and benzoic acid, in free or base addition salt form.

2. The product of claim 1 wherein the mouthwash is dispensed by pouring the mouthwash through the filter.

3. The product of claim 1, wherein the preservative is selected from methylparaben and sodium benzoate.

4. The product of claim 1 wherein the liquid formulation comprises an orally acceptable antiplaque agent.

5. The product of claim 4, wherein the orally acceptable antiplaque agent is selected from stannous, copper, magnesium and strontium salts, and mixtures thereof.

6. The product of claim 1 wherein the liquid formulation comprises a desensitizing agent.

7. The product of claim 6, wherein the desensitizing agent is selected from potassium chloride, potassium nitrate, strontium salts, and mixtures thereof.

8. The product of claim 1 wherein the liquid formulation comprises one or more antioxidants.

9. The product of claim 8, wherein the one or more antioxidants are selected from butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

10. The product of claim 1, wherein the filter is a filter comprising activated carbon or affinity beads or affinity matrix.

11. The product of claim 10, wherein the mouthwash is dispensed by pouring the mouthwash through the filter.

12. A method of dispensing a mouthwash from the mouthwash product of claim 1 comprising the step of filtering the mouthwash using the filter to remove the preservative just prior to use, and optionally adding to the mouthwash one or more sparingly soluble ingredients after filtering and just prior to use.

13. A method of tooth whitening or cleaning or of treating conditions of the oral cavity such as gingivitis, dental plaque or halitosis, or reducing demineralization of the enamel, comprising applying a mouthwash dispensed in accordance with claim 12 to the oral cavity.

14. The method of claim 12, wherein the filter is a filter comprising activated carbon or affinity beads or affinity matrix.

* * * * *